(12) United States Patent
Dinnell et al.

(10) Patent No.: US 8,283,365 B2
(45) Date of Patent: Oct. 9, 2012

(54) INDOLE MODULATORS OF THE ALPHA 7 NICOTINIC ACETYLCHOLINE RECEPTOR

(75) Inventors: Kevin Dinnell, Harlow (GB); Andrew P Lightfoot, Harlow (GB); Howard Robert Marshall, Harlow (GB)

(73) Assignee: Proximagen Limited, London (GB)

( * ) Notice: Subject to any disclaimer, the term of this patent is extended or adjusted under 35 U.S.C. 154(b) by 122 days.

(21) Appl. No.: 12/936,408

(22) PCT Filed: Apr. 16, 2009

(86) PCT No.: PCT/EP2009/054493
§ 371 (c)(1),
(2), (4) Date: Oct. 5, 2010

(87) PCT Pub. No.: WO2009/127678
PCT Pub. Date: Oct. 22, 2009

(65) Prior Publication Data
US 2011/0034515 A1    Feb. 10, 2011

(30) Foreign Application Priority Data

Apr. 17, 2008 (GB) .................................. 0807050.0
Jun. 4, 2008 (GB) .................................. 0810229.5

(51) Int. Cl.
*C07D 401/12* (2006.01)
*A61K 31/4439* (2006.01)
(52) U.S. Cl. ...................................... 514/339; 546/277.4
(58) Field of Classification Search ........................ None
See application file for complete search history.

(56) References Cited

FOREIGN PATENT DOCUMENTS

WO    WO 01/32619 A    5/2001
WO    WO 2005/079800 A    9/2005

*Primary Examiner* — Zinna Northington Davis
(74) *Attorney, Agent, or Firm* — Banner & Witcoff, Ltd.

(57) ABSTRACT

This invention relates to modulation of the α7 nicotinic acetylcholine receptor (nAChR) by a compound of formula (I) or a salt thereof

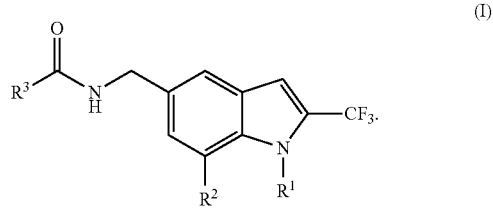

(I)

11 Claims, 2 Drawing Sheets

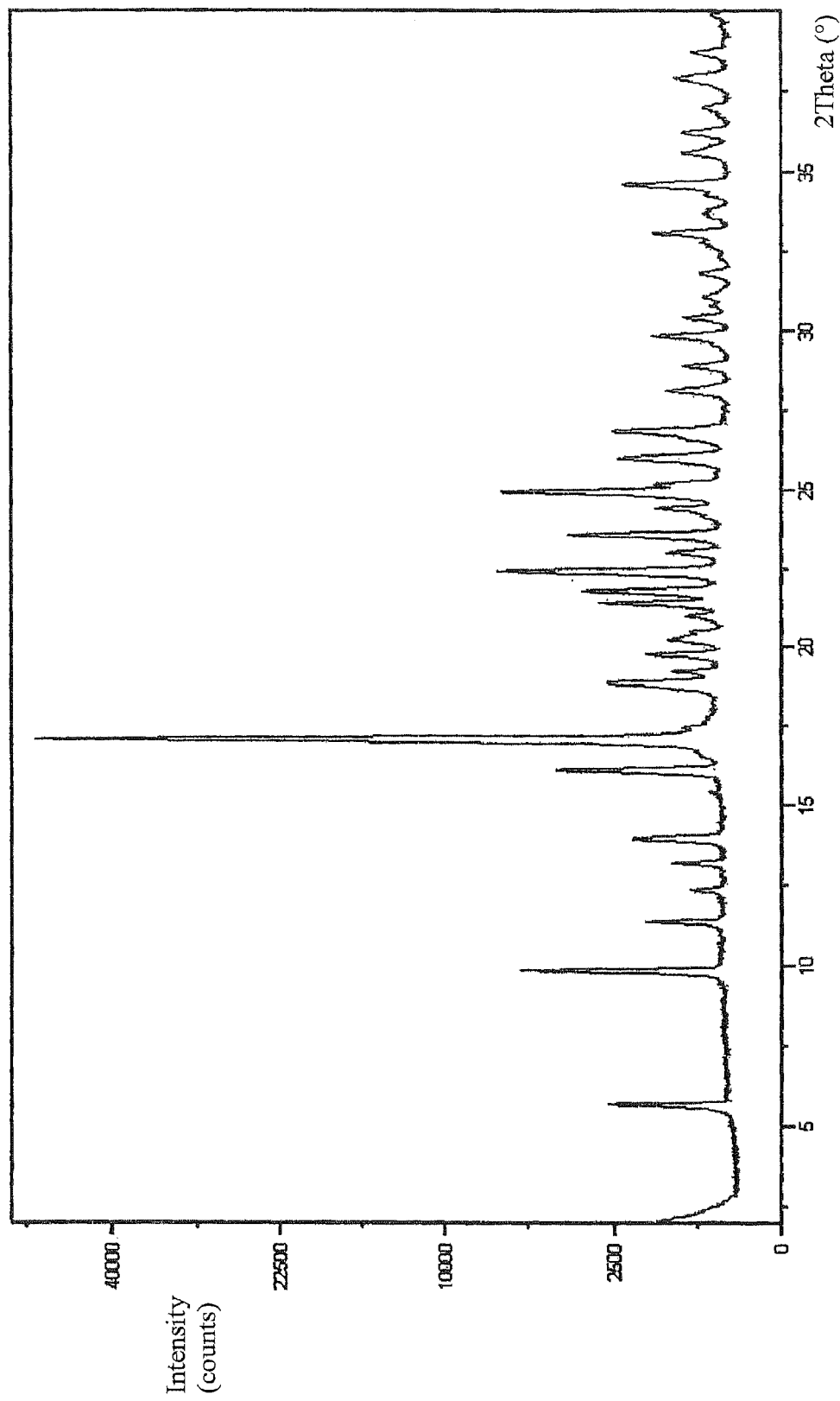
FIG. 1: XRPD pattern of Compound 1A

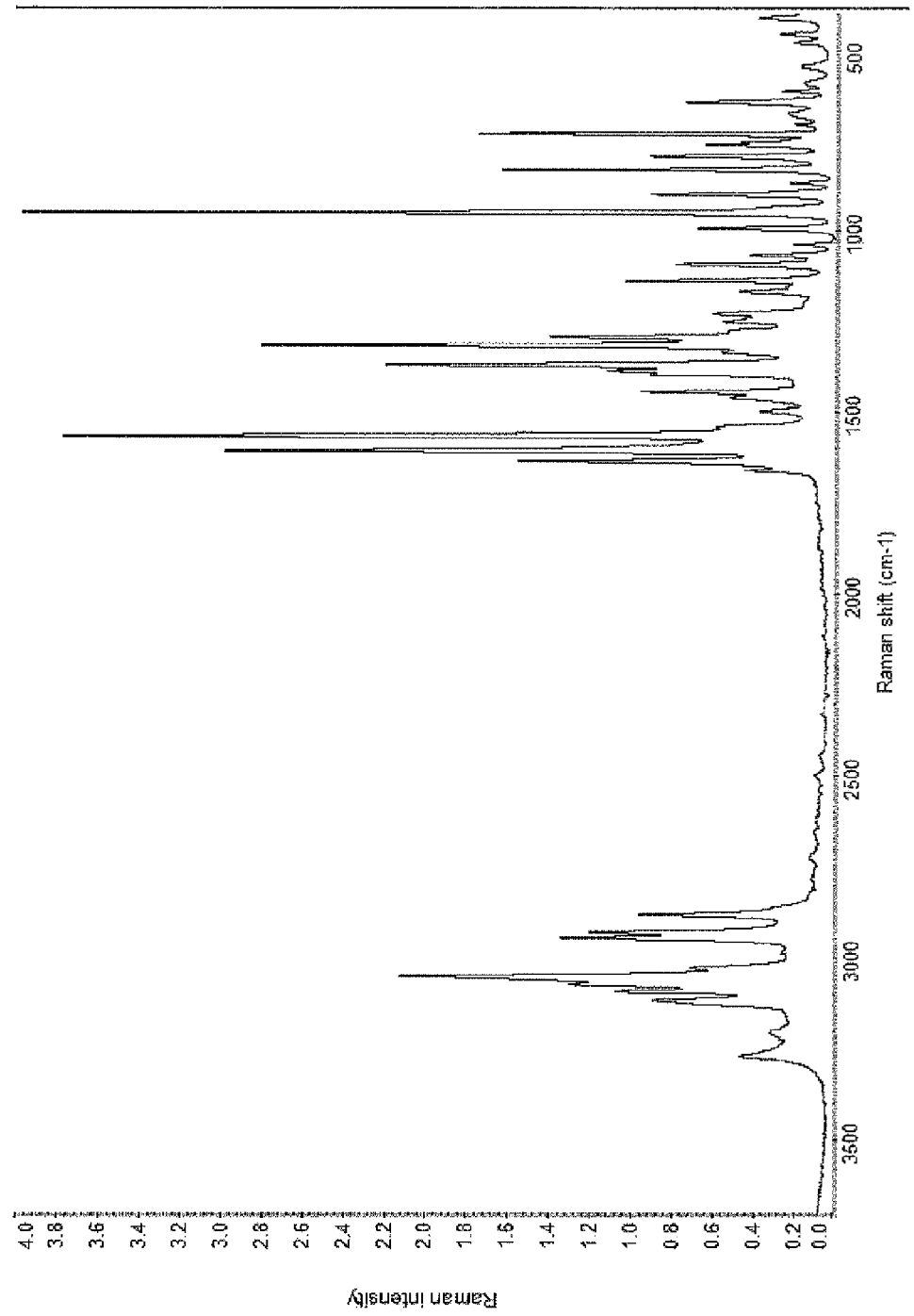

INDOLE MODULATORS OF THE ALPHA 7 NICOTINIC ACETYLCHOLINE RECEPTOR

CONTINUING DATA

This application is a 371 of International Application No. PCT/EP2009/054493, filed 16 Apr. 2009, which claims the priority of GB Application Nos. 0810229.5, filed 4 Jun. 2008, and 0807050.0, filed 17 Apr. 2008, which are incorporated herein in their entireties.

This invention relates to novel indole derivatives having activity in modulation of the α7 nicotinic acetylcholine receptor (nAChR). The invention also relates to the use of the derivatives in treating diseases and conditions mediated by modulation of the α7 nAChR. In addition, the invention relates to compositions containing the derivatives and processes for their preparation.

The neurotransmitter acetylcholine (ACh), by binding to cholinergic receptors causes the opening of ion channels within the mammalian system. The central nervous system (CNS) contains two types of ACh receptor, muscarinic receptors and nAChRs. nAChRs are ligand-gated ion channels containing five subunits (for reviews, see Colquhon et al. (1997) Advances in Pharmacology 39, 191-220; Williams et al. (1994) Drug News & Perspectives 7, 205-223; Doherty et al. (1995) Annual reports in Medicinal Chemistry 30, 41-50). The nAChR gene family can be divided into two groups: those coding for β subunits and those coding for α subunits (for reviews, see Karlin & Akabas (1995) Neuron 15, 1231-1244; Sargent (1993) Annu. Rev. Neurosci. 16, 403-443). Three of the α subunits, α7, α8 and α9, can form functional receptors when expressed alone and form homooligomeric receptors.

Studies have indicated that neuronal nicotinic receptors play important roles in modulating neurotransmission, cognition, sensory gating, and anxiety (Zarei et al. Neuroscience 1999, 88, 755-764, Frazier et al. J. Neurosci. 1998, 18, 8228-8235, Radcliffe et al. J. Neurosci. 1998, 18, 7075-7083, Minana et al. Neuropharmacology 1998, 37, 847-857, Albuquerque et al. Toxicol. Lett. 1998, 102-103, 211-218, Neubauer, et al. Neurology 1998, 51, 1608-1612, Stevens et al. Psychopharmacology 1998, 136, 320-327, Adler et al. Schizophrenia Bull. 1998, 24, 189-202.); thus, there has been interest in the use of compounds that modulate these receptors for treating CNS diseases.

A role for α7 receptors in the etiology of schizophrenia has been suggested by linkage studies (Freedman et al, Psychopharmacology (2004), 174(1), 54-64) demonstrating an association between the α7 locus and a sensory gating deficit which represents a major schizophrenia endophenotype. Such gating deficits in patients have been transiently reversed by nicotine with a pharmacology consistent with action via α7. In addition in animal models, lesion of forebrain cholinergic afferents or pharmacological blockade of α7 receptors elicits similar sensory gating deficits which are also apparent in in-bred mouse strains expressing reduced levels of the α7 receptor. Nicotine has been reported to normalise the deficits in both lesioned animals and in-bred mouse strains, again with a pharmacology compatible with activity at the α7 receptor. Pharmacological blockade of α7 receptors has been reported to impair rodent short-term working memory, whilst receptor activation has been reported to enhance performance in the same paradigm, thus implicating α7 receptors as a target for cognitive enhancement.

α7 nAChRs are characterised by their fast activation kinetics and high permeability to $Ca^{2+}$ compared to other subtypes (Delbono et al. J. Pharmacol. Exp. Ther. 1997, 280, 428-438.) and exhibit rapid desensitization following exposure to agonists. (Castro et al., Neurosci. Lett. 1993, 164, 137-140, Couturier et al., Neuron 1990, 5, 847-856, Alkondon et al., J. Pharmacol. Exp. Ther. 1994, 271, 494-506). Treatment with α7 agonists may therefore be problematic because both acetylcholine and nicotine both show activation followed by blockade and/or desensitisation of the receptor and hence chronic treatment with an agonist may well result in apparent antagonism. In addition, agonists have been shown to exhibit highest affinity for the desensitised state of the receptor and can, thus, mediate receptor desensitisation at concentrations below the threshold for receptor activation (Briggs and McKenna. Neuropharmacology 1998 37, 1095-1102).

This problem may be overcome by treatment with a positive allosteric modulator (PAM). PAMs enhance α7 nAChR activation mediated by endogenous or exogenous agonists without activating the receptor in their own right, i.e. in the absence of agonist. A number of PAMs have been reported (Lightfoot et al. Progress in medicinal chemistry 46:131-71, 2008)

According to a first aspect, the invention provides a compound of formula (I) or a salt thereof:

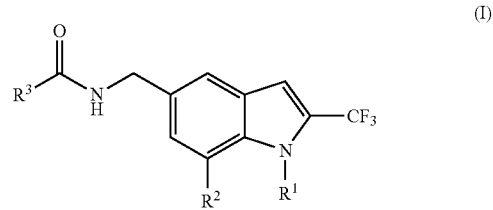

(I)

wherein
$R^1$ is hydrogen or $C_{1-3}$alkyl;
$R^2$ is hydrogen, halo or cyano; and
$R^3$ is the group

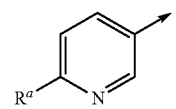

wherein $R^a$ is halo, $C_{1-6}$alkyl, $C_{1-6}$alkoxy, halo$C_{1-6}$alkyl, halo$C_{1-6}$alkoxy, cyano or di$C_{1-3}$alkylamino.

As used herein, a $C_{1-6}$alkyl substituent is a univalent radical derived by removal of a hydrogen atom from an acyclic $C_{1-6}$alkane. Such $C_{1-6}$alkyl substituents include methyl and ethyl, may be straight chain (i.e. n-propyl, n-butyl, n-pentyl and n-hexyl) or branched chain (for example, isopropyl, isobutyl, secbutyl, tert-butyl, isopentyl and neopentyl).

As used herein, a halo substituent refers to fluoro, chloro, bromo and iodo radicals. In an embodiment, unless otherwise indicated, any halo substituent is chloro or bromo.

As used herein, a halo$C_{1-6}$alkyl substituent is a $C_{1-6}$alkyl group substituted by one or more halo substituents, which halo substituents may be the same or different. Such $C_{1-6}$haloalkyl substituents include monofluoromethyl, difluoromethyl, trifluoromethyl and 1-chloro-2-fluoroethyl.

As used herein, a $C_{1-6}$alkoxy substituent is group of formula "R—O—" where R is $C_{1-6}$alkyl as defined above. Such alkoxy substituents include methoxy and ethoxy and may be straight chain (i.e. n-propoxy, n-butoxy, n-pentoxy and n-hexyloxy) or branched chain (for example, isopropoxy, isobutoxy, secbutoxy, tert-butoxy, isopentoxy and neopentoxy).

As used herein, a haloC$_{1-6}$alkoxy substituent is of formula "R$^x$—O—" where R$^x$ is C$_{1-6}$haloalkyl as defined above. Such C$_{1-6}$haloalkoxy substituents include monofluoromethoxy, difluoromethoxy, trifluoromethoxy and 1-chloro-2-fluoroethoxy and may be straight chain or branched chain.

In an embodiment, R$^1$ is hydrogen.

In an embodiment, R$^2$ is hydrogen.

In a further embodiment, R$^1$ and R$^2$ are hydrogen.

In an embodiment, R$^a$ is bromo, chloro, methyl, methoxy, ethoxy, trifluoromethyl, trifluoroethoxy or cyano.

In a further embodiment, R$^a$ is bromo, methyl, methoxy, ethoxy, trifluoromethyl, trifluoroethoxy or cyano.

In a further embodiment, R$^a$ is trifluoromethyl.

In an embodiment, the compound is selected from:

N-[(2-trifluoromethyl-1H-indol-5-yl)methyl]-6-(trifluoromethyl)-3-pyridinecarboxamide;

N-[(2-trifluoromethyl-1H-indol-5-yl)methyl]-6-(2,2,2-trifluoroethoxy)-3-pyridinecarboxamide;

6-bromo-N-{[2-(trifluoromethyl)-1H-indol-5-yl]methyl}-3-pyridinecarboxamide;

6-cyano-N-{[2-(trifluoromethyl)-1H-indol-5-yl]methyl}-3-pyridinecarboxamide;

N-[(2-trifluoromethyl-7-bromo-1H-indol-5-yl)methyl]-6-(trifluoromethyl)-3-pyridinecarboxamide;

N-[(2-trifluoromethyl-7-cyano-1H-indol-5-yl)methyl]-6-(trifluoromethyl)-3-pyridinecarboxamide;

N-[(1-methyl-2-trifluoromethylindol-5-yl)methyl]-6-(trifluoromethyl)-3-pyridinecarboxamide;

or a salt thereof.

In a further embodiment the compound is N-[(2-trifluoromethyl-1H-indol-5-yl)methyl]-6-(trifluoromethyl)-3-pyridinecarboxamide.

It will be appreciated that the present invention is intended to include compounds having any combination of the embodiments defined hereinbefore.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

The compounds of formula (I) may form pharmaceutically acceptable salts, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm. Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In one embodiment the salt of the compound of formula (I) is a pharmaceutically acceptable salt.

Hereinafter, the compounds of formula (I) and their pharmaceutically acceptable salts, are also referred to as "the compounds of the invention".

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "promoieties", for example as described by H. Bundgaard in "Design of Prodrugs" (the disclosure in which document is incorporated herein by reference) may be placed on appropriate functionalities when such functionalities are present within the compound defined in the first aspect.

The compounds of the invention are typically in solid form. In the solid state, the compounds of the invention may exist in crystalline or noncrystalline form, or as a mixture thereof. For a compound of the invention in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

The skilled artisan will further appreciate that the compounds of the invention in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

In one aspect, the present invention provides N-[(2-trifluoromethyl-1H-indol-5-yl)methyl]-5-(trifluoromethyl)-2-pyridinecarboxamide in crystalline form.

BRIEF DESCRIPTION OF THE DRAWINGS

FIG. 1 provides an XRPD pattern of crystalline N-[(2-trifluoromethyl-1H-indol-5-yl)methyl]-5-(trifluoromethyl)-2-pyridinecarboxamide.

FIG. 2 provides a Raman spectrum of crystalline N-[(2-trifluoromethyl-1H-indol-5-yl)methyl]-5-(trifluoromethyl)-2-pyridinecarboxamide.

In a further embodiment, the present invention provides crystalline N-[(2-trifluoromethyl-1H-indol-5-yl)methyl]-5-(trifluoromethyl)-2-pyridinecarboxamide characterised in that it provides an XRPD pattern comprising peaks substantially as set out in Table 1.

Therefore, according to a further aspect, the invention provides a solvate, hydrate, prodrug or polymorph of the compounds of the invention.

Certain compounds of the invention may exist in one or more tautomeric forms. All tautomers and mixtures thereof are included in the scope of the present invention.

Certain compounds of the invention may possess one or more chiral centres and so exist in a number of stereoisomeric forms. Compounds having one chiral centre may exist as enantiomers or a racemic mixture containing enantiomers. Compounds having two or more chiral centres may exist as diastereoismomers or enantiomers. All stereoisomers (for example enantiomers and diastereoisomers) and mixtures thereof are included in the scope of the present invention. Racemic mixtures may be separated to give their individual enantiomer using preparative HPLC using a column with a chiral stationary phase or resolved to yield individual enantiomers utilizing methods known to those skilled in the art. In addition, chiral intermediate compounds may be resolved and used to prepare individual enantiomers.

The invention also includes all suitable isotopic variations of the compounds of the invention. An isotopic variation of the compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, sulphur, fluorine and chlorine such as $^{2}H$, $^{3}H$, $^{13}C$, $^{14}C$, $^{15}N$, $^{17}O$, $^{18}O$, $^{35}S$, $^{18}F$ and $^{36}Cl$ respectively. Certain isotopic variations of the invention, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

Compounds of the invention may be prepared in a variety of ways. In the following reaction schemes and hereinafter, unless otherwise stated $R^1$ to $R^3$ are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic), etc. . . . (IVa), (IVb), (IVc) etc.

Compounds of formula (I) may be prepared according to scheme 1 by coupling compounds of formula (II) with compounds of formula (III). Typical conditions comprise treatment with a suitable coupling agent, such as HATU, HOBt, DCC in a suitable solvent such as DCM or DMF can be used. Alternative conditions comprise conversion of the carboxylic acid (II) to the corresponding acyl chloride, using oxalyl chloride in a suitable solvent (such as THF or DCM) with a suitable base (such as triethylamine).

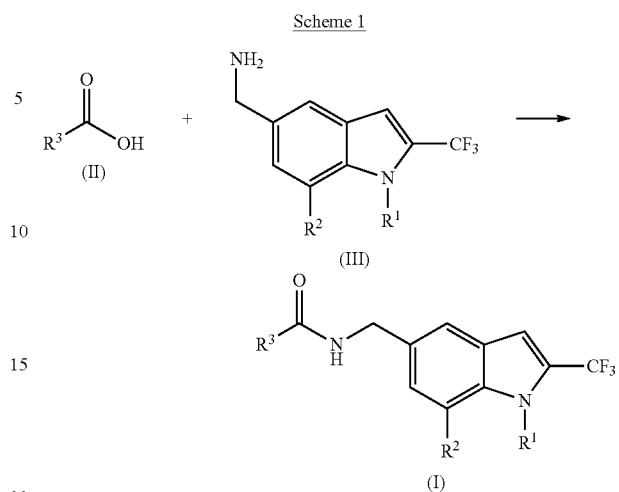

Scheme 1

Alternatively, compounds of formula (I) may be prepared from other compounds of formula (I).

For example, according to reaction scheme 2, compounds of formula (Ia) where $R^2$ is cyano, may be prepared from compounds of formula (Ib), where $R^2$ is bromo, by reaction with zinc cyanide with a suitable catalyst in a suitable solvent.

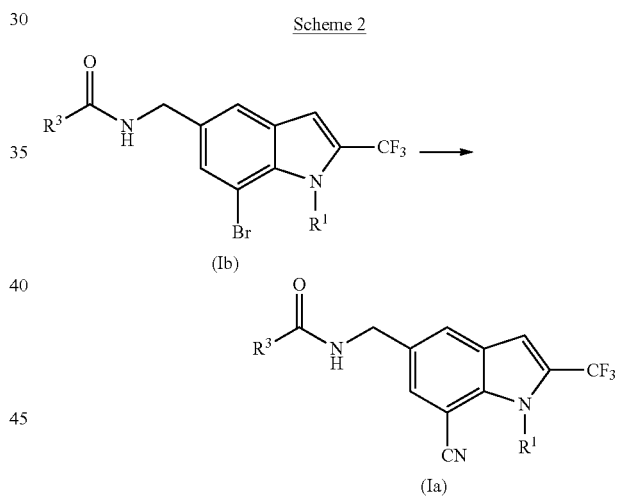

Scheme 2

Compounds of formula (IIIa), i.e. compounds of formula (III) where $R^1$ is hydrogen, may be prepared according to scheme 3. Treatment of compounds of formula (IV) with trifluoroacetic anhydride in the presence of a base (such as triethylamine) in a suitable solvent (such as DCM) gives compounds of formula (V). Halogenation of compounds of formula (V) with a suitable radical halogen source such as sulfuryl chloride or N-bromosuccinimide in a suitable solvent (such as carbon tetrachloride) gives compounds of formula (VI). Treating compounds of formula (VI) with a phosphine derivative (such as triphenylphosphine) gives compounds of formula (VII), which may be cyclised to give compounds of formula (VIII). Typical cyclisation conditions comprise heating in a suitable solvent (such as DMF) to a temperature in excess of 100° C. Compounds of formula (III) are obtained by reduction of compounds of formula (VIII) with borane or nickel borohydride.

Scheme 3

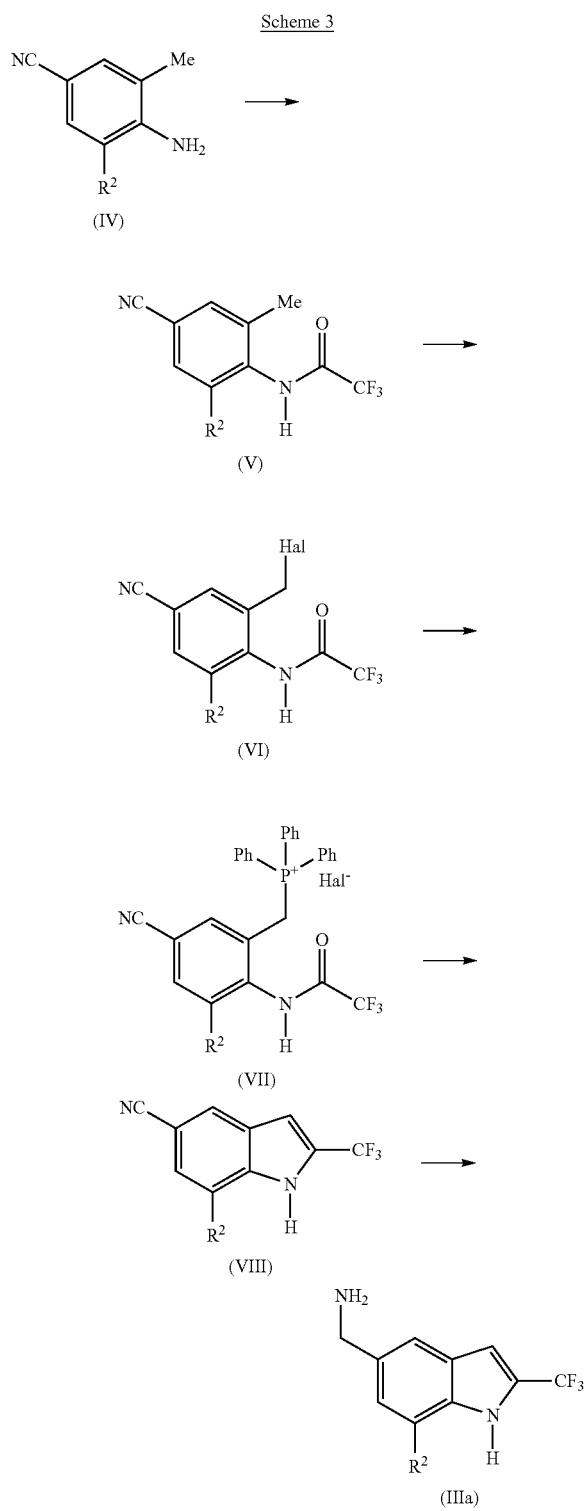

Scheme 4

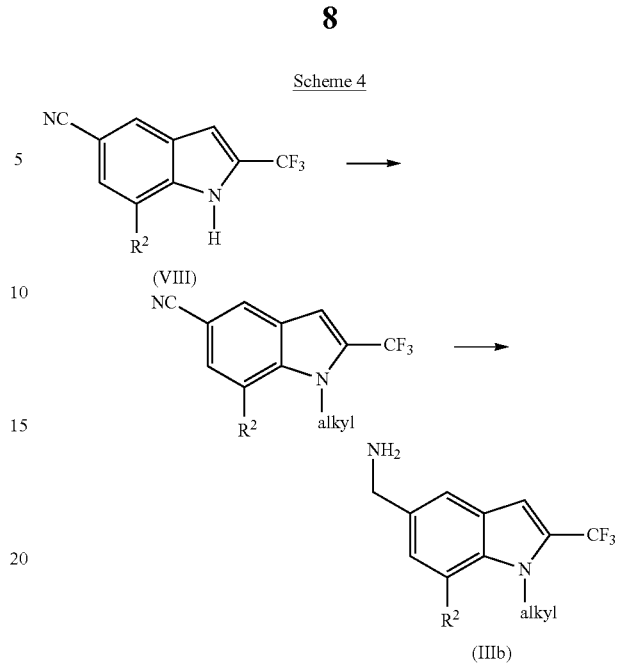

Compounds of formula (IIIb), i.e. compounds of formula (III) where $R^1$ is $C_{1-3}$alkyl, may be prepared according to reaction scheme 4 by reacting compounds of formula (VIII) with a suitable alkyl halide (such as methyl iodide) in the presence of a base (such as sodium hydride) in a suitable solvent (such as DMF) followed by reduction using borane or nickel borohydride.

Salts may be prepared conventionally by reaction with the appropriate acid or acid derivative.

The compounds of the invention may be useful for the treatment of diseases and conditions mediated by positive allosteric modulation of the α7 nAChR or diseases and conditions which are associated with modulation of the α7 nAChR. Diseases or conditions mediated by positive allosteric modulation of the α7 nAChR or diseases and conditions which are associated with modulation of the α7 nAChR include (the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10):

i) Psychotic disorders for example Schizophrenia (including the subtypes Paranoid Type (295.30), Disorganised Type (295.10), Catatonic Type (295.20), Undifferentiated Type (295.90) and Residual Type (295.60)); Schizophreniform Disorder (295.40); Schizoaffective Disorder (295.70) (including the subtypes Bipolar Type and Depressive Type); Delusional Disorder (297.1) (including the subtypes Erotomanic Type, Grandiose Type, Jealous Type, Persecutory Type, Somatic Type, Mixed Type and Unspecified Type); Brief Psychotic Disorder (298.8); Shared Psychotic Disorder (297.3); Psychotic Disorder due to a General Medical Condition (including the subtypes with Delusions and with Hallucinations); Substance-Induced Psychotic Disorder (including the subtypes with Delusions (293.81) and with Hallucinations (293.82)); and Psychotic Disorder Not Otherwise Specified (298.9).

ii) cognitive impairment including for example the treatment of impairment of cognitive functions including attention, orientation, learning disorders, memory (i.e. memory disorders, amnesia, amnesic disorders, transient global amnesia syndrome and age-associated memory impairment) and language function; as well as cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to other diseases such as schizophrenia, bipolar disorder, depression and other psychiatric disorders, and post-electro-convulsive treatment related cognitive disorders; and dyskinetic disorders such as Parkinson's disease, neuroleptic-induced parkinsonism, and tardive dyskinesias.

iii) Depression and mood disorders for example Depressive Episodes (including Major Depressive Episode, Manic Episode, Mixed Episode and Hypomanic Episode); Depressive Disorders (including Major Depressive Disorder, Dysthymic Disorder (300.4), Depressive Disorder Not Otherwise Specified (311)); Bipolar Disorders (including Bipolar I Disorder, Bipolar II Disorder (i.e. Recurrent Major Depressive Episodes with Hypomanic Episodes) (296.89), Cyclothymic Disorder (301.13) and Bipolar Disorder Not Otherwise Specified (296.80)); Other Mood Disorders (including Mood Disorder due to a General Medical Condition (293.83) which includes the subtypes With Depressive Features, With Major Depressive-like Episode, With Manic Features and With Mixed Features); Substance-Induced Mood Disorder (including the subtypes With Depressive Features, With Manic Features and With Mixed Features); and Mood Disorder Not Otherwise Specified (296.90).

iv) Anxiety disorders for example Social Anxiety Disorder; Panic Attack; Agoraphobia, Panic Disorder; Agoraphobia Without History of Panic Disorder (300.22); Specific Phobia (300.29) (including the subtypes Animal Type, Natural Environment Type, Blood-Injection-Injury Type, Situational Type and Other Type); Social Phobia (300.23); Obsessive-Compulsive Disorder (300.3); Posttraumatic Stress Disorder (309.81); Acute Stress Disorder (308.3); Generalized Anxiety Disorder (300.02); Anxiety Disorder Due to a General Medical Condition (293.84); Substance-Induced Anxiety Disorder; and Anxiety Disorder Not Otherwise Specified (300.00).

v) Substance-related disorders for example Substance Use Disorders (including Substance Dependence, Substance Craving and Substance Abuse); Substance-Induced Disorders (including Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders (including Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9)); Amphetamine (or Amphetamine-Like)-Related Disorders (for example Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9)); Caffeine Related Disorders (including Caffeine Intoxication (305.90), Caffeine-Induced Anxiety Disorder, Caffeine-Induced Sleep Disorder and Caffeine-Related Disorder Not Otherwise Specified (292.9)); Cannabis-Related Disorders (including Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9)); Cocaine-Related Disorders (including Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9)); Hallucinogen-Related Disorders (including Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9)); Inhalant-Related Disorders (including Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9)); Nicotine-Related Disorders (including Nicotine Dependence (305.1), Nicotine Withdrawal (292.0) and Nicotine-Related Disorder Not Otherwise Specified (292.9)); Opioid-Related Disorders (including Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9)); Phencyclidine (or Phencyclidine-Like)-Related Disorders (including Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9)); Sedative-, Hypnotic-, or Anxiolytic-Related Disorders (including Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9)); Polysubstance-Related Disorder (including Polysubstance Dependence (304.80)); and Other (or Unknown) Substance-Related Disorders (including Anabolic Steroids, Nitrate Inhalants and Nitrous Oxide).

vi) Sleep disorders for example primary sleep disorders such as Dyssomnias (including Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47)); primary sleep disorders such as Parasomnias (including Nightmare Disorder (307.47), Sleep Terror Disorder (307.46), Sleepwalking Disorder (307.46) and Parasomnia Not Otherwise Specified (307.47)); Sleep Disorders Related to Another Mental Disorder (including Insomnia Related to Another Mental Disorder (307.42) and Hypersomnia Related to Another Mental Disorder (307.44)); Sleep Disorder Due to a General Medical Condition; and Substance-Induced Sleep Disorder (including the subtypes Insomnia Type, Hypersomnia Type, Parasomnia Type and Mixed Type).

vii) Eating disorders such as Anorexia Nervosa (307.1) (including the subtypes Restricting Type and Binge-Eating/Purging Type); Bulimia Nervosa (307.51) (including the subtypes Purging Type and Nonpurging Type); Obesity; Compulsive Eating Disorder; Binge Eating Disorder; and Eating Disorder Not Otherwise Specified (307.50).

viii) Autism Spectrum Disorders including Autistic Disorder (299.00), Asperger's Disorder, Rett's Disorder, Childhood Disintegrative Disorder and Pervasive Developmental Disorder Not Otherwise Specified.

ix) Attention-Deficit/Hyperactivity Disorder (including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9)); Hyperkinetic Disorder; Disruptive Behaviour Disorders such as Conduct Disorder (including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

x) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

xi) Sexual dysfunctions such as Sexual Desire Disorders (including Hypoactive Sexual Desire Disorder (302.71) and Sexual Aversion Disorder (302.79)); sexual arousal disorders (including Female Sexual Arousal Disorder (302.72) and Male Erectile Disorder (302.72)); orgasmic disorders (including Female Orgasmic Disorder (302.73), Male Orgasmic Disorder (302.74) and Premature Ejaculation (302.75)); sexual pain disorder (including Dyspareunia (302.76) and Vaginismus (306.51)); Sexual Dysfunction Not Otherwise Specified (302.70); paraphilias (including Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9)); gender identity disorders (including Gender Identity Disorder in Children (302.6) and Gender Identity Disorder in Adolescents or Adults (302.85)); and Sexual Disorder Not Otherwise Specified (302.9).

The compounds of the invention may also be useful in treating inflammation, inflammatory pain, rheumatoid arthritis and sepsis.

In one embodiment, the patient is a human. The term "treatment" includes prophylaxis, treatment of symptoms and/or treatment of the underlying causes of symptoms where this is appropriate for the relevant condition(s).

Thus in one aspect, the present invention provides a compound of formula (I) as hereinbefore described or a salt thereof for use as a medicament.

In one aspect, the present invention provides a compound of formula (I) as hereinbefore described or a salt thereof for use in treating a disease which is associated with a reduction in function of $\alpha 7$ nicotinic acetylcholine receptor.

In one aspect, the present invention provides a compound of formula (I) as hereinbefore described or a salt thereof for use in treating a disease which benefits from positive allosteric modulation of the $\alpha 7$ nicotinic acetylcholine receptor.

In one aspect, the present invention provides a compound of formula (I) as hereinbefore described or a salt thereof for use as a positive allosteric modulator of the $\alpha 7$ nicotinic acetylcholine receptor.

In another aspect, the invention provides a compound of formula (I) as hereinbefore described or a salt thereof for use in the treatment of a psychotic disorder. In one embodiment, the invention provides a compound of formula (I) as hereinbefore described or a salt thereof for use in the treatment of schizophrenia. In one embodiment, the invention provides a compound of formula (I) as hereinbefore described or a salt thereof for use in the treatment of anxiety or depression.

The invention also provides a compound of formula (I) as hereinbefore described or a salt thereof for use in the treatment of cognitive impairment.

The invention also provides a compound of formula (I) as hereinbefore described or a salt thereof for use in the treatment of Alzheimer's disease.

In another aspect, the invention provides the use of a compound of formula (I) as hereinbefore described or a salt thereof in the manufacture of a medicament for treating a disease which is associated with a reduction in function of $\alpha 7$ nicotinic acetylcholine receptor.

In another aspect, the invention provides the use of a compound of formula (I) as hereinbefore described or a salt thereof in the manufacture of a medicament for use in treating a disease which benefits from positive allosteric modulation of the $\alpha 7$ nicotinic acetylcholine receptor.

In another aspect, the invention provides the use of a compound of formula (I) as hereinbefore described or a salt thereof in the manufacture of a medicament for the positive allosteric modulation of the $\alpha 7$ nicotinic acetylcholine receptor.

In another aspect, the invention provides the use of a compound of formula (I) as hereinbefore described or a salt thereof in the manufacture of a medicament for use in the treatment of a psychotic disorder.

In another aspect, the invention provides the use of a compound of formula (I) as hereinbefore described or a salt thereof in the manufacture of a medicament for use in the treatment of schizophrenia.

In another aspect, the invention provides the use of a compound of formula (I) as hereinbefore described or a salt thereof in the manufacture of a medicament for use in the treatment of anxiety or depression.

In another aspect, the invention provides the use of a compound of formula (I) as hereinbefore described or a salt thereof in the manufacture of a medicament for use in the treatment of cognitive impairment.

In another aspect, the invention provides the use of a compound of formula (I) as hereinbefore described or a salt thereof in the manufacture of a medicament for use in the treatment of Alzheimer's disease.

In another aspect, the invention provides a method of treating a disease which is associated with a reduction in function of α7 nicotinic acetylcholine receptor, which comprises administering to a human in need thereof an effective amount of a compound of formula (I) as hereinbefore described or a salt thereof.

In one aspect, the present invention provides a method of treating a disease which benefits from positive allosteric modulation of the α7 nicotinic acetylcholine receptor, which comprises administering to a human in need thereof an effective amount of a compound of formula (I) as hereinbefore described or a salt thereof.

In one aspect, the present invention provides a method for the positive allosteric modulation of the α7 nicotinic acetylcholine receptor, which comprises administering to a human an effective amount of a compound of formula (I) as hereinbefore described or a salt thereof.

In another aspect, the invention provides a method for use in treating a psychotic disorder, which comprises administering to a human in need thereof an effective amount of a compound of formula (I) as hereinbefore described or a salt thereof.

In one embodiment, the invention provides a method for treating schizophrenia, which comprises administering to a human in need thereof an effective amount of a compound of formula (I) as hereinbefore described or a salt thereof.

In one embodiment, the invention provides a method for treating anxiety or depression, which comprises administering to a human in need thereof an effective amount of a compound of formula (I) as hereinbefore described or a salt thereof.

The invention also provides a method for treating cognitive impairment, which comprises administering to a human in need thereof an effective amount of a compound of formula (I) as hereinbefore described or a salt thereof.

The invention also provides a method for treating Alzheimer's disease, which comprises administering to a human in need thereof an effective amount of a compound of formula (I) as hereinbefore described or a salt thereof.

In general, compounds of formula (I) or a salt thereof may be administered in doses ranging from about 0.1 mg to about 1000 mg per day, in single or divided doses (i.e., from 1 to 4 doses per day), although variations will necessarily occur depending upon the species, weight, age and condition of the subject being treated, as well as the particular route of administration chosen. In an embodiment, the dose is administered once daily. In an embodiment, the dosage level is in the range of about 0.1 mg/kg to about 500 mg/kg body weight per day. In a further embodiment, the dosage level is in the range of about 0.1 mg/kg to about 100 mg/kg body weight per day.

The compounds of formula (I) and their salts thereof may also be suitable for combination with other actives, such as typical and atypical antipsychotics, mood stabilisers, antidepressants, anxiolytics, drugs for extrapyramidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a salt thereof and at least one antipsychotic agent, a mood stabiliser, an antidepressant, an anxiolytic, a drug for extrapyramidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a salt thereof may be administered as adjunctive therapeutic treatment to patients who are receiving administration of at least one antipsychotic agent, a mood stabiliser, an antidepressant, an anxiolytic, a drug for extrapyramidal side effects or a cognitive enhancer, but the scope of the invention also includes the adjunctive therapeutic administration of at least one antipsychotic agent, a mood stabiliser, an antidepressant, an anxiolytic, a drug for extrapyramidal side effects or a cognitive enhancer to patients who are receiving administration of compounds of formula (I) or a salt thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of a compound of formula (I) or a salt thereof to a patient receiving therapeutic administration of at least one antipsychotic agent. In a further aspect, the invention provides the use of a compound of formula (I) or a salt thereof in the manufacture of a medicament for adjunctive therapeutic administration for the treatment of a psychotic disorder in a patient receiving therapeutic administration of at least one antipsychotic agent. The invention further provides a compound of formula (I) or a salt thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of a compound of formula (I) or a salt thereof. In a further aspect, the invention provides the use of at least one antipsychotic agent in the manufacture of a medicament for adjunctive therapeutic administration for the treatment of a psychotic disorder in a patient receiving therapeutic administration of a compound of formula (I) or a salt thereof. The invention further provides at least one antipsychotic agent for adjunctive therapeutic administration for the treatment of a psychotic disorder in a patient receiving therapeutic administration of a compound of formula (I) or a salt thereof.

In a further aspect, the invention provides a method of treatment of a psychotic disorder by simultaneous therapeutic administration of a compound of formula (I) or a salt thereof in combination with at least one antipsychotic agent. The invention further provides the use of a combination of a compound of formula (I) or a salt thereof and at least one antipsychotic agent in the manufacture of a medicament for simultaneous therapeutic administration in the treatment of a psychotic disorder. The invention further provides the use of a compound of formula (I) or a salt thereof in the manufacture of a medicament for simultaneous therapeutic administration with at least one antipsychotic agent in the treatment of a psychotic disorder. The invention further provides a compound of formula (I) or a salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with a compound of formula (I) or a salt thereof in the treatment of a psychotic disorder.

In a further aspect, the invention provides a kit-of-parts for use in the treatment of a psychotic disorder comprising a first dosage form comprising a compound of formula (I) or a salt thereof and one or more further dosage forms each comprising an antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyramidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyramidal side effects and a cognitive enhancer in the manufacture of a medicament for adjunctive therapeutic administration for the treatment of a psychotic disorder in a patient receiving therapeutic administration of a compound of the present invention.

The invention also provides the use of an active ingredient selected from the group consisting of: a mood stabiliser, an antidepressant, an anxiolytic, a drug for extrapyramidal side effects and a cognitive enhancer for adjunctive therapeutic administration for the treatment of a psychotic disorder in a patient receiving therapeutic administration of a compound of the present invention.

In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyramidal side effects and a cognitive enhancer.

The invention further provides the use of a combination of a compound of the present invention and an active ingredient selected from the group consisting of: a mood stabiliser, an antidepressant, an anxiolytic, a drug for extrapyramidal side effects and a cognitive enhancer in the manufacture of a medicament for simultaneous therapeutic administration in the treatment of a psychotic disorder.

The invention further provides the use of a combination of a compound of the present invention and an active ingredient selected from the group consisting of: a mood stabiliser, an antidepressant, an anxiolytic, a drug for extrapyramidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of an active ingredient selected from the group consisting of: a mood stabiliser, an antidepressant, an anxiolytic, a drug for extrapyramidal side effects and a cognitive enhancer in the manufacture of a medicament for simultaneous therapeutic administration with a compound of the present invention in the treatment of a psychotic disorder.

The invention further provides the use of an active ingredient selected from the group consisting of: a mood stabiliser, an antidepressant, an anxiolytic, a drug for extrapyramidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyramidal side effects and a cognitive enhancer for simultaneous therapeutic administration.

Examples of antipsychotic drugs that may be useful in the present invention include, but are not limited to: sodium channel blockers; mixed 5HT/dopamine receptor antagonists;

mGluR5 positive modulators; D3 antagonists; 5HT6 angatonists; nicotinic alpha-7 modulators; glycine transporter GlyT1 inhibitors; D2 partial agonist/D3 antagonist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL™, from Mylan, Zenith Goldline, UDL, Novartis); olanzapine (available under the tradename ZYPREXA™, from Lilly; ziprasidone (available under the tradename GEODON™, from Pfizer); risperidone (available under the tradename RISPERDAL™, from Janssen); quetiapine fumarate (available under the tradename SEROQUEL™, from AstraZeneca); sertindole (available under the tradename SERLECT™); amisulpride (available under the tradename SOLION™, from Sanofi-Synthelabo); haloperidol (available under the tradename HALDOL™, from Ortho-McNeil); haloperidol decanoate (available under the tradename HALDOL Decanoate™; haloperidol lactate (available under the tradenames HALDOL™ and INTENSOLT™); chlorpromazine (available under the tradename THORAZINE™, from SmithKline Beecham (GSK); fluphenazine (available under the tradename PROLIXIN™, from Apothecon, Copley, Schering, Teva, and American Pharmaceutical Partners, Pasadena); fluphenazine decanoate (available under the tradename PROLIXIN Decanoate™); fluphenazine enanthate (available under the tradename PROLIXIN™); fluphenazine hydrochloride (available under the tradename PROLIXIN™); thiothixene (available under the tradename NAVANE™; from Pfizer); thiothixene hydrochloride (available under the tradename NAVANET™); trifluoperazine (10-[3-(4-methyl-1-piperazinyl)propyl]-2-(trifluoromethyl)phenothiazine dihydrochloride, available under the tradename STELAZINE™, from SmithKline Beckman; perphenazine (available under the tradename TRILAFON™; from Schering); perphenazine and amitriptyline hydrochloride (available under the tradename ETRAFON TRILAFON™); thioridazine (available under the tradename MELLARIL™; from Novartis, Roxane, HiTech, Teva, and Alpharma); molindone (available under the tradename MOBAN™, from Endo); molindone hydrochloride (available under the tradename MOBAN™); loxapine (available under the tradename LOXITANET™; from Watson); loxapine hydrochloride (available under the tradename LOXITANET™); and loxapine succinate (available under the tradename LOXITANE™). Furthermore, benperidol (Glianimon™), perazine (Taxilan™) or melperone (Eunerpan™) may be used.

Other suitable antipsychotic drugs include promazine (available under the tradename SPARINE™), triflurpromazine (available under the tradename VESPRIN™) chlorprothixene (available under the tradename TARACTAN™), droperidol (available under the tradename INAPSINE™), acetophenazine (available under the tradename TINDALT™), prochlorperazine (available under the tradename COMPAZINET™), methotrimeprazine (available under the tradename NOZINAN™), pipotiazine (available under the tradename PIPOTRIL™), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, aripiprazole, haloperidol, clozapine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, aminepitine, radafaxine, mianserin, mirtazapine, nefazodone and trazodone).

Anxiolytics which may be used in the therapy of the present invention include V1b antagonists, $5HT_7$ antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic M1 agonists (such as cevimeline).

In one embodiment, the active ingredient for use in combination with a compound of the present invention, is an atypical antipsychotic, for example clozapine, olanzapine, risperidone, quetiapine, aripirazole, ziprasidone or amisulpride.

In one embodiment, the active ingredient for use in combination with a compound of the present invention is a typical antipsychotic, for example chlorpromazine, thioridazine, mesoridazine, fluphenazine, perphenazine, prochlorperazine, trifluoperazine, thiothixine, haloperidol, thiflurpromazine, pimozide, droperidol, chlorprothixene, molindone or loxapine.

In another embodiment, the active ingredient for use in combination with a compound of the present invention is a mood stabiliser, for example lithium, sodium valproate/valproic acid/divalproex, carbamazepine, lamotrigine, gabapentin, topiramate, oxcarbazepine or tiagabine.

In another embodiment, the active ingredient for use in combination with a compound of the present invention is an antidepressant, for example a serotonin agonist (such as rauwolscine, yohimbine or metoclopramide); a serotonin reuptake inhibitor (such as citalopram, escitalopram, fluoxetine, fluvoxamine, femoxetine, indalpine, zimeldine, paroxetine or sertraline); a dual serotonin/noradrenaline reuptake inhibitor (such as venlafaxine, reboxetine, duloxetine or milnacipran); a noradrenaline reuptake inhibitors (such as reboxetine); a tricyclic antidepressants (such as amitriptyline, clomipramine, imipramine, maprotiline, nortriptyline or trimipramine); a monoamine oxidase inhibitor (such as isocarboxazide, moclobemide, phenelzine or tranylcypromine); or other (such as bupropion, amineptine, radafaxine, mianserin, mirtazapine, nefazodone or trazodone). In another embodiment, the active ingredient for use in combination with a compound of the present invention is an anxiolytic, for example a benzodiazepine such as alprazolam or lorazepam.

For use in medicine, the compounds of the present invention are usually administered as a standard pharmaceutical composition. The present invention therefore provides in a further aspect a pharmaceutical composition comprising a compound of formula (I) as hereinbefore described or a salt thereof and a pharmaceutically acceptable carrier or excipient. The pharmaceutical composition can be for use in the treatment of any of the conditions described herein.

The compounds of the invention may be administered by any convenient method, for example by oral, parenteral (e.g. intravenous), buccal, sublingual, nasal, rectal or transdermal administration and the pharmaceutical compositions adapted accordingly.

The compounds of the invention which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device.

Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

The composition may be in unit dose form such as a tablet, capsule or ampoule. Each dosage unit for oral administration may contain, for example, from 1 to 500 mg (and for parenteral administration contains, for example, from 0.1 to 50 mg) of a compound of the formula (I) or a salt thereof calculated as the free base. In an embodiment the unit dose for oral administration contains from 50 to 450 mg. In a further embodiment the unit dose contains from 100 to 400 mg.

In order to obtain consistency of adjunctive administration, the compositions of each of the components, or of the combination of the components is, for example, in the form of a unit dose.

Supporting Compounds

The preparation of a number of compounds of the invention are described below.

In the procedures that follow, after each starting material, reference to an intermediate is typically provided. This is provided merely for assistance to the skilled chemist. The starting material may not necessarily have been prepared from the batch referred to.

Compounds of the invention and intermediates are named using ACD/Name PRO6.02 chemical naming software (Advanced Chemistry Development Inc., Toronto, Ontario, M5H2L3, Canada).

ABBREVIATIONS

TEA Triethylamine
TFA Trifluoroacetic acid
TFAA Trifluoroacetic acid anhydride
DAD Diode Array Detector
LC/MS Liquid Chromatography/Mass Spectrometry
NMR Nuclear Magnetic Resonance
THF Tetrahydrofuran
DMSO Dimethylsulfoxide
DMF Dimethylformamide
DCM/MDC Dichloromethane/Methylene dichloride
CDI 1,1'-Carbonyldiimidazole
EDC 1-ethyl-3-(dimethylaminopropyl)carbodiimide
HOAt 1-hydroxy-7-azabenzotriazole
HOBt 1-hydroxybenzotriazole
Pd on C Palladium on Charcoal
MeCN Acetonitrile
MDAP Mass-directed auto-preparation
Cy Cyclohexane
EtOAc Ethyl acetate
ES electrospray
ES-API electrospray-atmospheric pressure ionisation
Min minutes
Me methyl
Et ethyl degC degree Celsius
SCX strong cationic exchange
SAX strong anionic exchange
h hour(s)
DIPEA N,N-diisopropylethylamine
HATU O-(7-Azabenzotriazol-1-yl)-N,N,N',N'-tetramethyluronium hexafluorophosphate
NBS N-bromosuccinimide
DCC Dicyclohexylcarbodiimide Starting materials were obtained from commercial suppliers and used without further purification unless otherwise stated. Flash chromatography was carried out using pre-packed Isolute Flash™ or Biotage™ silica-gel columns as the stationary phase and analytical grade solvents as the eluent unless otherwise stated.

NMR spectra were obtained at 298K, 303.2K or 300K, at the frequency stated using either a Bruker™ DPX400 or AV400 machine and run as a dilute solution of $CDCl_3$ unless otherwise stated. All NMR spectra were reference to tetramethylsilane (TMS $\delta_H$ 0, $\delta_C$ 0). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet).

Total ion current traces were obtained for electrospray positive and negative ionisation (ES+/ES−) and/or atmospheric pressure chemical positive and negative ionisation (AP+/AP−).

Where appropriate, these retention times were used as a guide for purification using mass-directed auto-purification (MDAP).

Purification

A number of the compounds were purified using a Mass Directed Auto-Purification System (MDAP) incorporating HPLC techniques and an appropriate mass spectrometer such as the Waters® ZQ mass spectrometer.

Intermediate 1: N-(4-cyano-2-methylphenyl)-2,2,2-trifluoroacetamide

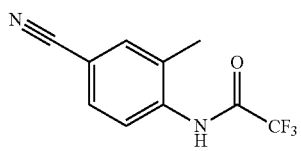

In a round-bottomed flask 4-amino-3-methylbenzonitrile (Alfa Aesar, Avocado, Lancaster; 10.88 g, 82 mmol), and $Et_3N$ (22.95 mL, 165 mmol) were stirred in DCM (200 mL) at 0° C. TFAA (13.95 mL, 99 mmol) was added slowly via a dropping funnel and the mixture stirred at room temperature for 30 min. The reaction mixture was poured into 2M HCl (150 mL). The organic layer was then collected and then washed with a saturated solution of sodium bicarbonate (150 mL), dried ($MgSO_4$), filtered and the solvent was removed to give a dark yellow solid (19.37 g);

m/z (ES−) 227 (M−1); $^1$H NMR (400 MHz, $CDCl_3$): δ 8.43 (1H, d), 7.91 (1H, br s), 7.59 (1H, dd), 7.56 (1H, s), 2.37 (3H, s).

Intermediate 2: ({5-Cyano-2-[(trifluoroacetyl)amino]phenyl}methyl)(triphenyl)phosphonium chloride

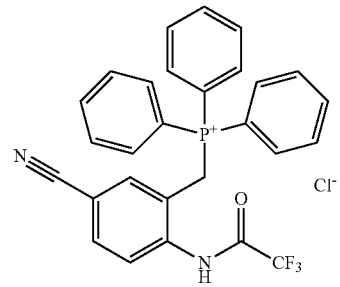

In a round-bottomed flask N-(4-cyano-2-methylphenyl)-2,2,2-trifluoroacetamide (Intermediate 1, 19.37 g, 85 mmol), sulfuryl dichloride (27.6 mL, 340 mmol) and diphenylperoxyanhydride (1.028 g, 4.24 mmol) were heated in carbon tetrachloride (210 mL) at 100° C. for 3 h. The mixture was cooled to room temperature and then the reaction mixture was poured into 2M HCl (350 mL). The organic layer was then collected and the solvent was removed to give N-[2-(chloromethyl)-4-cyanophenyl]-2,2,2-trifluoroacetamide as an orange oil, (25.54 g) which was used in the next step without further purification. This oil was added to triphenylphosphine (26.2 g, 100 mmol) and the mixture was heated in toluene (300 mL) at 110° C. for 3 h. The mixture was cooled to room temperature overnight and the precipitate was filtered and washed with small amounts of toluene and diethyl ether to give the title compound as an off-white solid (29.91 g);

m/z (ES+) 489; $^1$H NMR (400 MHz, $CDCl_3$): δ 12.32 (1H, s), 7.79-7.57 (16H, m), 7.50 (1H, d), 7.38 (1H, s), 6.18 (2H, d).

Intermediate 3: 2-Trifluoromethyl-1H-indole-5-carbonitrile

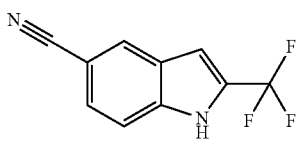

({5-Cyano-2-[(trifluoroacetyl)amino]phenyl}methyl)(triphenyl)phosphonium chloride (Intermediate 2, 50.41 g, 95 mmol) was heated in DMF (180 mL) at 140° C. for 7 h. The mixture was cooled to room temperature and the solvents were evaporated. This residue was combined with the corresponding residue from another experiment (wherein Intermediate 2, 7.9 g, 15.05 mmol was heated in DMF (50 mL) at 155° C. for 2 h). The combined residues were azeotroped with toluene (100 mL×2). The resulting residue was treated with diethyl ether (500 mL) and the precipitate filtered and washed with diethyl ether (100 mL). The filtrate was evaporated and the resulting orange oil (~60 g) was dissolved in DCM (200 mL) and stirred at room temperature. Iso-hexane was added until the cloudyness remained (~400 mL) and the mixtured stirred for 3 days. No precipitate was observed so the mixture was evaporated and chromatographed (Biotage 75L, eluting with dichloromethane) to give the title compound as a colourless solid (21.7 g);

m/z (ES⁻) 209 (M−1); ¹H NMR (400 MHz, CDCl₃): δ 8.85 (1H, br s), 8.08 (1H, s), 7.57 (1H, d), 7.53 (1H, d), 7.03 (1H, s).

Intermediate 3A:
2-(trifluoromethyl)-1H-indole-5-carbonitrile

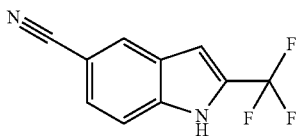

5-cyano-2-(trifluoromethyl)-1H-indole-3-carboxylic acid (Intermediate 13, 2.09 g) was dissolved in NMP (10 mL) and H₂O (1 mL) was then added. The mixture was heated to 130-140° C. overnight under nitrogen. The solution was cooled to room temperature and H₂O (30 mL) was added and the solution stirred for 40 min. and then filtered. The cake was washed with H₂O. The product is then dried under vacuum at 40° C. to give the title compound (1.42 g);

¹H NMR (300 MHz, d6 DMSO) δ 8.26 (1H, s), 7.64 (2H, s), 7.18 (1H, s).

Intermediate 4:
[(2-Trifluoromethyl-1H-indol-5-yl)methyl]amine

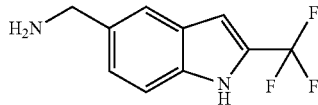

A solution of 2-trifluoromethyl-1H-indole-5-carbonitrile (Intermediate 3, 0.16 g, 0.761 mmol) in tetrahydrofuran (5 mL) cooled in an ice-water bath, was treated with a 1M solution of borane tetrahydrofuran complex (3.05 mL, 3.05 mmol) dropwise via syringe. The reaction mixture was then left to stir under argon for 18 hrs while allowing it to warm to room temperature. The reaction mixture was then quenched with methanol (10 mL) and stirred at room temperature for 10 min. The reaction mixture was then poured onto a SCX cartridge (10 g) and washed well with methanol. The desired product was then eluted using 2M ammonia/methanol solution. Evaporation to dryness gave the title compound which was used in the next step without further purification.

Intermediate 5:
[(2-Trifluoromethyl-1H-indol-5-yl)methyl]amine hydrochloride

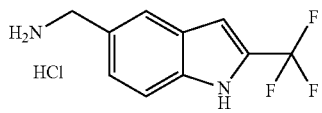

A solution of 2-(trifluoromethyl)-1H-indole-5-carbonitrile (Intermediate 3, 21.7 g, 103 mmol) in THF (300 mL), cooled in an ice-water bath, was treated with borane tetrahydrofuran complex (250 mL, 250 mmol) added dropwise via a dropping funnel. The mixture was stirred under argon for 5 h while allowing to warm to room temperature. The mixture was then stirred for a further 18 h at room temperature. Methanol (100 mL) was added dropwise and the mixture was then stirred for 20 mins at room temperature. The solvents were removed and the residue was dissolved in methanol (300 mL). The mixture was then heated to reflux for 1 h. The mixture was cooled to room temperature and HCl/ether (1M, 200 mL) was added and the solvents evaporated. The residue was triturated with diethyl ether (2×200 mL). The residue was slurried in DCM (50 mL) and diethyl ether (300 mL) and a further portion HCl in ether (1M, 100 mL) was added. The mixture was then filtered under Ar and the solid dried in a vacuum oven to give the title compound as a colourless solid (21.7 g);

m/z (ES⁻) 213 (M−1); ¹H NMR (400 MHz, d⁶ DMSO): δ 12.45 (1H, br s), 8.35 (3H, br s), 7.79 (1H, s), 7.53 (1H, d), 7.42 (1H, dd), 7.08 (1H, s), 4.09 (2H, q).

Intermediate 5A: {[2-(trifluoromethyl)-1H-indol-5-yl]methyl}amine hydrochloride

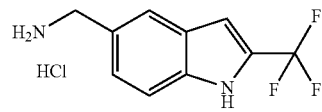

2-(trifluoromethyl)-1H-indole-5-carbonitrile (Intermediate 3A, 25 g), PtO₂.H₂O (3%, 750 mg) and MeOH (175 mL) were added to a hydrogenation flask. 4M HCl in dioxane (89 mL) was added and the reaction vessel is purged with N₂ and then H₂. The mixture was hydrogenated at 60 psi of H₂ and 17-23° C. for 24 hrs. The mixture was filtered through celite and then through a 0.2 μm PTFE filter. MP-TMT resin (15 wt %) was then added and the slurry was stirred for 3 hrs at 40° C., cooled to 17-23° C., and then filtered through a pad of celite. The celite pad and resin were washed with MeOH (100 mL). The solution was concentrated to a minimum by vacuum distillation and n-propanol (200 mL) was added and concentrated to a minimum. Toluene (200 mL) was added and then cyclohexane (75 mL) and the slurry was allowed to stir for 2 hrs at 17-23° C. The mixture was then cooled to 0-5° C. and allowed to stir for 2 hrs. The solid was filtered and washed with toluene to give the title compound (25.3 g);

¹H NMR (300 MHz, d6 DMSO) δ 8.55 (3H, s), 7.80 (1H, s), 7.53 (1H, d), 7.45 (1H, d), 7.05 (1H, s), 4.07 (2H, s).

Intermediate 6: N-[2-(Bromomethyl)-4-cyanophenyl]-2,2,2-trifluoroacetamide

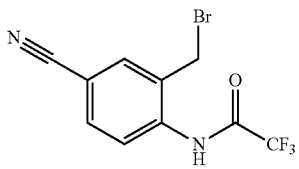

In a 500 mL round-bottomed flask N-(4-cyano-2-methylphenyl)-2,2,2-trifluoroacetamide (Intermediate 1; 7.3 g, 32.0 mmol), NBS (5.98 g, 33.6 mmol), and benzoyl peroxide (70%) (1.162 g, 4.80 mmol) were added to carbon tetrachloride (150 mL). The reaction mixture was then heated to reflux under argon for 4 days. The reaction mixture was cooled to room temperature then NBS (0.5 eq, 3 g) and benzoyl peroxide (0.075 eq, 0.581 g) were added. The reaction mixture was then heated to reflux for a further 18 hrs. The reaction mixture was allowed to cool to room temperature then poured into 2M NaOH (100 mL). The organic layer was collected then washed with a solution of sodium metabisulfite (10 g in 100 mL water), dried (MgSO$_4$), filtered and the solvent removed. The resulting orange oil was then purified through a plug of silica gel eluting with 1-10% EtOAc:isoHexane. The desired fractions were then combined and evaporated to dryness to give a 1:1 mixture of the title compound and the starting material as an orange solid (9 g) which was then used in the next step without further purification.

Intermediate 7: ({5-Cyano-2-[(trifluoroacetyl)amino]phenyl}methyl)(triphenyl)phosphonium bromide

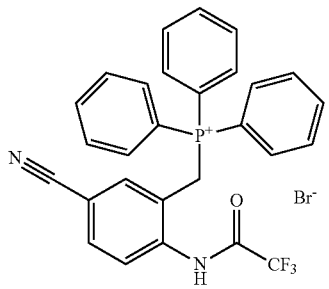

In a 250 mL round-bottomed flask N-[2-(bromomethyl)-4-cyanophenyl]-2,2,2-trifluoroacetamide (Intermediate 6, 6 g, 19.54 mmol) was dissolved in toluene (100 mL). Triphenylphosphine (5.12 g, 19.54 mmol) was added and the reaction mixture heated to 85° C. under argon for 5 hrs. The reaction mixture was allowed to cool to room temperature and the resulting yellow solid was collected, washed well with toluene, to give the title compound as a yellow solid (6.5 g); m/z (ES+) 489; $^1$H NMR (400 MHz, d$_6$-DMSO): δ 11.19 (1H, s), 7.79-7.57 (17H, m), 7.39 (1H, s), 5.25 (2H, d).

Intermediate 8: 2-(Trifluoromethyl)-5-cyano-7-bromo-1H-indole

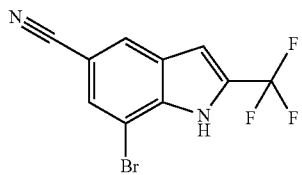

({5-Cyano-2-[(trifluoroacetyl)amino]phenyl}methyl)(triphenyl)phosphonium bromide (Intermediate 7, 32 g) was dissolved in DMF (150 mL) and decolorising charcoal (32 g) was added. The reaction mixture was stirred at room temperature for 2 hrs. The reaction mixture was then filtered washing with DMF (100 mL). N-Bromosuccinimide (34.9 g) was then added to the filtrate and the reaction mixture was then stirred at room temperature overnight. The reaction mixture was quenched with a saturated solution of sodium metabisulfite (500 mL) and stirred at room temperature for 30 min. The reaction mixture was then extracted with ethyl acetate (2×400 mL) and the organic extracts where combined, dried (MgSO$_4$), filtered and the solvent was removed to give ({3-bromo-5-cyano-2-[(trifluoroacetyl)amino]phenyl}methyl)(triphenyl)phosphonium bromide as a crude product which was then used in the next reaction without further purification (37.2 g);
m/z (ES$^+$) 568 & 570 (M+1).

({3-bromo-5-cyano-2-[(trifluoroacetyl)amino]phenyl}methyl)(triphenyl)phosphonium bromide (37.2 g, crude) was dissolved in DMF (150 mL) and the reaction mixture was heated to 130° C. stirring for 3 hrs. The reaction mixture was allowed to cool to room temperature then quenched with water (400 mL). The reaction mixture was then extracted with ethyl acetate (3×300 mL). The organic extract was washed with a 1:1 mixture of water:brine (2×600 mL), dried (MgSO$_4$), filtered and the solvent was removed. The resulting residues were then purified by filtration through a pad of silica gel eluting with 2-10% EtOAc: isoHexane to give the title compound as an off-white solid (6 g);
m/z (ES$^-$) 287+289 (M-1); $^1$H NMR (400 MHz, d$_6$-DMSO): δ 13.15 (1H, s), 8.32 (1H, s), 8.01 (1H, s), 7.34 (1H, s).

Intermediate 9: [(2-Trifluoromethyl-7-bromo-1H-indol-5-yl)methyl]amine

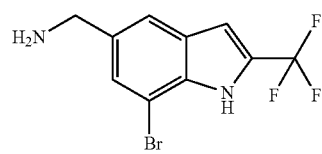

A solution of 2-(trifluoromethyl)-5-cyano-7-bromo-1H-indole (Intermediate 8; 200 mg, 0.692 mmol) in THF (10 mL) cooled in an ice-water bath was treated with borane tetrahydrofuran complex (1M in THF, 1.522 mL, 1.522 mmol) dropwise via a syringe and stirred under argon for 18 hrs while allowing to warm to room temp. The reaction mixture was then quenched with methanol (5 mL) and stirred at room temperature for 10 min. The reaction mixture was then evaporated to dryness to give the title compound as a white foam (230 mg), which was used in the next step without further purification;
m/z 290/292 (M−H).

Intermediate 10: 1-Methyl-2-Trifluoromethyl-5-cyanoindole

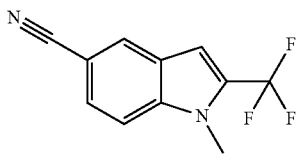

Sodium hydride (60% in mineral oil) (76 mg, 1.903 mmol) was added to 2-trifluoromethyl-1H-indole-5-carbonitrile (Intermediate 3, 200 mg, 0.952 mmol) stirred in DMF (5 mL) under argon at room temperature. The reaction mixture was stirred at room temperature for 30 min and iodomethane (0.119 mL, 1.903 mmol) was then added. The reaction mixture was left to stir for a further 1 h. The reaction mixture was poured into water (50 mL) and extracted with ethyl acetate (50 mL). The organic extract was washed with 1:1 water: Brine (50 mL×2), dried (MgSO$_4$), filtered and the solvent removed to give the title compound (290 mg) which was then used in the next reaction without further purification; $^1$H NMR (400 MHz, CDCl$_3$): δ 8.05 (1H, d), 7.59 (1H, dd), 7.46 (1H, d), 7.03 (1H, s), 3.90 (3H, s); m/z 225 (M+H).

Intermediate 11: {[1-Methyl-2-(trifluoromethyl)-1H-indol-5-yl]methyl}amine

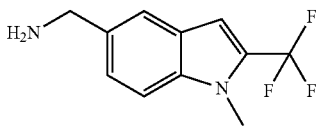

A solution of 1-methyl-2-trifluoromethyl-5-cyanoindole (Intermediate 10, 240 mg, 1.071 mmol) in THF (10 mL) cooled to 0° C. was treated with borane tetrahydrofuran complex (1M solution) (2.36 mL, 2.36 mmol) dropwise via a syringe and stirred under argon for 24 hrs.

The reaction mixture was quenched with methanol (5 mL) and stirred at room temperature for 10 min. The reaction mixture was evaporated to dryness to give the title compound crude as a white foam (300 mg), which was used in the next step without further purification.

Intermediate 12:
N-(4-cyano-2-iodophenyl)-2,2,2-trifluoroacetamide

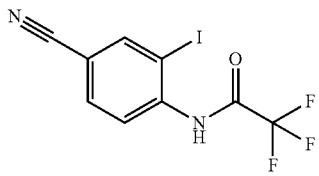

To a round bottomed flask equipped with an addition funnel, thermometer, reflux condenser, and nitrogen inlet were added 4-cyano-2-iodoaniline (7.88 g), acetonitrile (24 mL), and triethylamine (4.5 mL). Trifluoroacetic anhydride (5.0 mL) was added to the suspension while maintaining the temperature below 35-40° C. Note: exothermic addition is addition-rate controlled. The reaction was stirred for 30 min, diluted with water (31.5 mL). Note: initial portion of addition is exothermic and is addition-rate controlled. The slurry was held at 15-20° C. for 60 min. The product was isolated by filtration. The solid was washed with 80% aqueous acetonitrile, and dried in vacuo to give the title compound as a colorless solid (9.9 g);

$^1$H NMR (300 MHz, CDCl$_3$) δ 8.49 (1H, br s), 8.45 (1H, d), 8.15 (1H, s), 7.75 (1H, d).

Intermediate 13:
5-cyano-2-(trifluoromethyl)-1H-indole-3-carboxylic acid

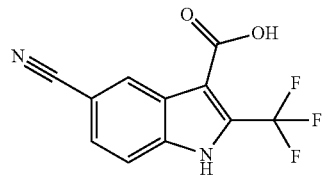

Cs$_2$CO$_3$ (95.82 g), CuI (3.36 g), and L-proline (9.06 g) were added to a 1 L reaction vessel. The vessel was purged with N$_2$. DMSO (80 mL) was then added to the reaction vessel and the contents are stirred at 18-23° C. for 10 minutes. N-(4-cyano-2-iodophenyl)-2,2,2-trifluoroacetamide (Intermediate 12, 40 g) was then added to a separate vessel and was dissolved in DMSO (40 mL). The solution of Intermediate 12 was then added to the reaction vessel over a period of at least 15 minutes as to control the CO$_2$ off-gassing. The reaction solution was stirred for 10 minutes. To the reaction mixture was then added tert-butyl acetoacetate (19.5 mL) The reaction solution was heated to 85-90° C. and stirred for 1 hr. To the reaction was then added an additional 0.5 equiv. of the tert-butyl acetoacetate.

The reaction was then stirred for an additional 1 hr. To the reaction was then added an additional 0.5 equiv. of the tert-butyl acetoacetate and the reaction was stirred overnight. Upon completion of the reaction, the contents in the vessel were cooled to 18-23° C. H$_2$O (160 mL) was added over a period of 15 minutes while maintaining the reaction temperature below 35° C. Then isopropyl acetate (160 mL) and toluene (320 mL) was added followed by H$_2$O (160 mL). The aqueous layer was drained, and the organic layer washed with saturated NH$_4$Cl solution (200 mL). The organic layer was then reduced to a minimum by vacuum distillation. DCM (160 mL) was added, and the contents were adjusted to 18-23° C. Trifluoroacetic acid (34.95 mL) was added over a period of 15 minutes. The solution was stirred overnight. The solid was filtered and washed with DCM (2×80 mL). The solid was dried in the vacuum oven to give the title compound (15.1 g);

$^1$H NMR (300 MHz, d6 DMSO) δ 8.48 (1H, s), 7.67 (2H, s).

Compound 1: N-[(2-Trifluoromethyl-1H-indol-5-yl) methyl]-6-(trifluoromethyl)-3-pyridinecarboxamide

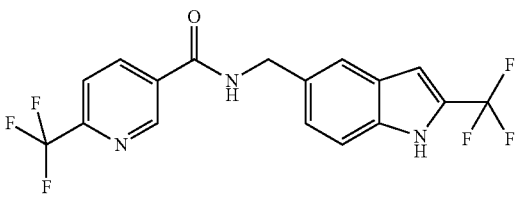

6-(Trifluoromethyl)nicotinic acid (Sigma-Aldrich; 178 mg, 0.934 mmol) was stirred in DCM (10 mL). Oxalyl chloride (0.131 mL, 1.494 mmol) then DMF (2.89 µl, 0.037 mmol) were added and the reaction mixture was left to stir at room temperature for 2 hrs under Argon. The reaction mixture was evaporated to dryness and the resulting residue was dissolved in DCM (10 mL). A solution of [(2-trifluoromethyl-1H-indol-5-yl)methyl]amine (Intermediate 4, 160 mg, 0.747 mmol) in DCM (10 mL) was added followed by triethylamine (0.208 mL, 1.494 mmol). The reaction mixture was left to stir at room temperature for 1 h. The reaction mixture was evaporated to dryness and the resulting residues where purified by MDAP to give the title compound (176 mg);

m/z (ES$^+$) 388 (M+1); $^1$H NMR (400 MHz, d4MeOD): δ 9.35 (1H, d), 8.43 (1H, dd), 8.12 (1H, d), 7.67 (1H, s), 7.43 (1H, d), 7.33 (1H, dd), 6.86 (1H, s), 4.69 (2H, s).

Compound 1A: N-[(2-Trifluoromethyl-1H-indol-5-yl)methyl]-6-(trifluoromethyl)-3-pyridinecarboxamide

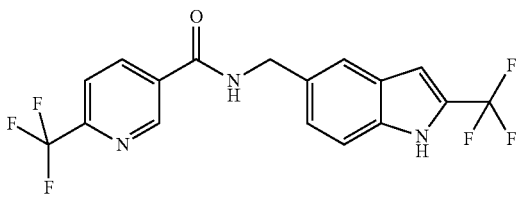

{[2-(trifluoromethyl)-1H-indol-5-yl]methyl}amine hydrochloride (Intermediate 5A, 646 g, 71% free amine equivalent), 6-trifluormethylnicotinic acid (429.7 g), diisopropylethylamine (1500 mL) and tetrahydrofuran (5.1 L) were placed in a flask equipped with an addition funnel, thermometer, and nitrogen inlet. The mixture was stirred vigorously for 10-15 min. The mixture was cooled to ~5° C. and propylphosphonic anhydride (3.2 L of 50 wt % solution) added slowly. The mixture was stirred at ~15° C. for 2 hrs. The mixture was cooled to ~5° C. and quenched by the addition of water (505 mL) slowly. The pH was adjusted to 5-6 by adding 20 wt % K$_3$PO$_4$ (2.9 L). The mixture was diluted with EtOAc (3.2 L) and the temperature adjusted to 15-20° C. The phases were separated and the organic mixture was washed sequentially with water (1.5 L) and then 5 wt % sodium bicarbonate solution (2.6 L). The mixture was filtered and the solvent removed to minimum volume under vacuum. Isopropyl alcohol (2.0 L) was added and the mixture filtered, and the solvent removed under vacuum two times. Isopropyl alcohol (980 mL) was added and the mixture heated to 70-80° C. Water (1.5 L) was added while maintaining temperature above 65° C. and monitoring turbidity. The temperature was adjusted to 65° C., seeded with product (4.5 g) and the mixture held at 65° C. for 30 min. The mixture was cooled to ~5° C. overnight and the product was isolated by filtration, washing the solids with cold 10% IPA in water (1 L), then dried in a vacuum oven to give the title compound (529 g);

$^1$H NMR (300 MHz, d6 DMSO) δ 12.24 (1H, s), 9.48 (1H, s), 9.22 (1H, s), 8.52 (1H, s), 8.05 (1H, s), 7.66 (1H, s), 7.47 (1H, d), 7.32 (1H, d), 7.00 (1H, s), 4.60 (2H, s).

Compound 1A was characterised as follows:

X-Ray Powder Diffraction (XRPD)

X-ray powder diffraction analysis was carried out using Cu K.alpha. radiation on Phillips X' pert Pro powder diffractometer, Model PW3040 Pro equipped with a Phillips X'Celerator RTMS (Real Time Multi Strip) detector. Data were collected in real time over a theta-two theta continuous scan at 32 sec/0.00167 degree/step from 2 degrees 2.theta. to 40 degrees 2.theta. The tube voltage and current were 40 kV and 40 mA The XRPD pattern is shown in FIG. 1. Characteristic XRPD angles are recorded in the Table 1 below. The margin of error is approximately ±0.2° 2θ for each of the peak assignments. Peak positions were measured using PANalytical X'Pert Highscore Plus software.

TABLE 1

| Position 2θ/° (±0.2° 2θ) |
|---|
| 5.7 |
| 9.8 |
| 16.1 |
| 17.1 |
| 22.5 |
| 23.6 |
| 24.9 |
| 34.5 |

Raman

The Raman spectrum of Compound 1A was recorded with the sample placed on an Al coated microscope slide using a Nicolet 960 E.S.P. FT-Raman spectrometer, at 4 cm$^{-1}$ resolution with excitation from a Nd:VO4 laser (1064 nm) with a power output of 433 mW.

The Raman spectrum is shown in FIG. 2. Bands were observed at: 3270, 3205, 3116, 3091, 3072, 3050, 3028, 2944, 2929, 2881, 1660, 1634, 1604, 1564, 1496, 1458, 1442, 1394, 1368, 1333, 1315, 1291, 1248, 1228, 1166. 1135, 1090, 1066, 1035, 991, 947, 897, 865, 829, 793, 762, 731, 705, 675, 643, 613, 590, 547, 478, 454, 411, 374, 325, 280, 272, 242, 221, cm$^{-1}$.

Compound 2: N-[(2-Trifluoromethyl-1H-indol-5-yl)methyl]-6-(2,2,2-trifluoroethoxy)-3-pyridinecarboxamide

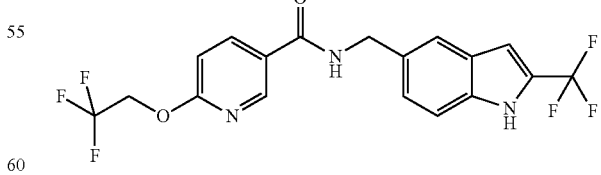

Prepared from 6-(2,2,2-trifluoroethoxy)pyridine-3-carboxylic acid (Apollo Scientific) and [(2-trifluoromethyl-1H-indol-5-yl)methyl]amine (Intermediate 4) according to the method as described of Compound 1; m/z (ES$^+$) 418 (M+1); $^1$H NMR (400 MHz, d6-DMSO): δ 12.21 (1H, s), 9.16 (1H, t), 8.74 (1H, s), 8.27 (1H, dd), 7.62 (1H, s), 7.44 (1H, d), 7.30 (1H, dd), 7.08 (1H, dd), 7.00 (1H, s), 5.06 (2H, m), 4.57 (2H, d).

Compound 3: 6-bromo-N-{[2-(Trifluoromethyl)-1H-indol-5-yl]methyl}-2-Pyridinecarboxamide

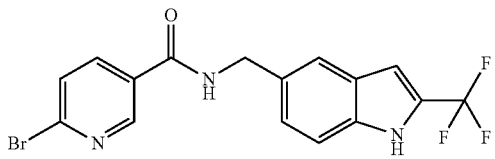

A mixture of {[2-(trifluoromethyl)-1H-indol-5-yl]methyl}amine hydrochloride (Intermediate 5, 1 g, 3.99 mmol), 6-bromo-3-pyridinecarboxylic acid (Matrix Scientific; 0.887 g, 4.39 mmol), EDC (0.841 g, 4.39 mmol), HOBT (0.672 g, 4.39 mmol) and DIPEA (2.8 mL, 16.03 mmol) in DCM (50 mL) was stirred at room temperature for 18 hrs. The mixture was stirred well with saturated aqueous NaHCO$_3$ solution, the organics separated and the aqueous further extracted (EtOAC×3). The combined organics were dried (Phase-Sep cartridge) and evaporated under reduced pressure to a white solid. Trituration with diethyl ether overnight and filtration afforded a crude white solid (1.16 g). A portion (88 mg) was further purified via MDAP to afford the title compound as a white solid (54 mg);

m/z [M+H]$^+$396/398 (M+1); $^1$H NMR (400 MHz, d4MeOD): δ 8.79 (1H, d), 8.10 (1H, dd), 7.70 (1H, dd), 7.64 (1H, s), 7.42 (1H, d), 7.30 (1H, d), 6.86 (1H, s), 4.66 (2H, s).

Compound 4: 6-Cyano-N-{[2-(Trifluoromethyl)-1H-indol-5-yl]methyl}-3-pyridinecarboxamide

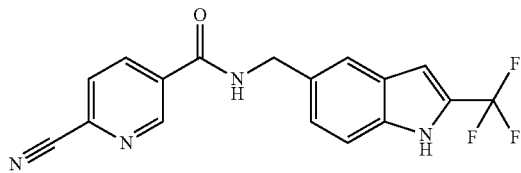

The title compound was prepared by a similar procedure to that described for Compound 3 using the appropriate carboxylic acid with 2-(trifluoromethyl)-1H-indol-5-yl]methyl}amine hydrochloride (Intermediate 5):

m/z [M+H]$^+$345 (M+1); $^1$H NMR (400 MHz, d4MeOD): δ 9.13 (1H, m), 8.39 (1H, dd), 7.99 (1H, dd), 7.68 (1H, s), 7.46 (1H, d), 7.34 (1H, d), 6.88 (1H, s), 4.70 (2H, s).

Compound 5: N-[(2-Trifluoromethyl-7-bromo-1H-indol-5-yl)methyl]-6-(trifluoromethyl)-3-Pyridinecarboxamide

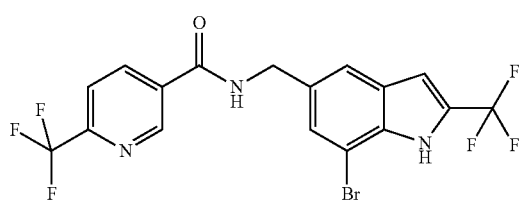

[(2-Trifluoromethyl-7-bromo-1H-indol-5-yl)methyl]amine (Intermediate 9, 230 mg, 0.785 mmol) was dissolved in DCM (10 mL) and 6-(trifluoromethyl)nicotinoyl chloride (ABCR; 181 mg, 0.863 mmol) was added. Et$_3$N (0.219 mL, 1.570 mmol) was added and the reaction mixture was then left to stir at room temperature for 30 min. The reaction mixture was quenched with water then the organic layer was collected, dried (MgSO$_4$), filtered and evaporated to dryness. The resulting residues were purified by MDAP to give the title compound, (200 mg);

m/z (ES$^+$) 466 & 468 (M+1); $^1$H NMR (400 MHz, CDCl$_3$): δ 9.08 (1H, d), 8.58 (1H, s), 8.33 (1H, dd), 7.82-7.76 (1H, m), 7.64 (1H, s), 7.52 (1H, s), 6.99 (1H, s), 6.53 (1H, m), 4.76 (2H, d).

Compound 6: N-[(2-Trifluoromethyl-7-cyano-1H-indol-5-yl)methyl]-6-(trifluoromethyl)-3-Pyridinecarboxamide

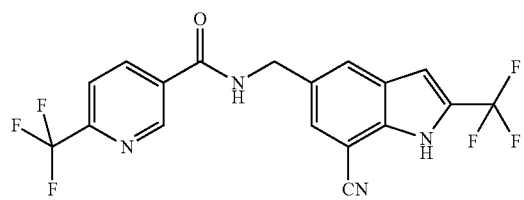

In a 5 mL microwave reactor vial N-[(2-Trifluoromethyl-7-bromo-1H-indol-5-yl)methyl]-5-(trifluoromethyl)-2-pyridinecarboxamide (Compound 5, 50 mg, 0.107 mmol), zinc cyanide (37.8 mg, 0.322 mmol), and Pd(Ph$_3$P)$_4$ (12.39 mg, 10.73 μmol) were dissolved in DMF (2.5 mL) and de-gassed using argon. The reaction mixture was then heated in a microwave reactor at 150° C. for 30 min. The reaction mixture was poured into water (20 mL) and extracted with ethyl acetate (50 mL). The organic extract was then washed with 1:1 mixture of water and brine (20 mL×2), dried (MgSO$_4$), filtered and the solvent removed. The resulting residues were purified by MDAP and evaporated to dryness to give the title compound as a white solid (35 mg);

m/z (ES$^+$) 413 (M+1); $^1$H NMR (400 MHz, d6-DMSO): δ 13.25 (1H, s), 9.51 (1H, t), 9.20 (1H, s), 8.51 (1H, dd), 8.08-8.03 (2H, m), 7.85 (1H, s), 7.23 (1H, s), 4.64 (2H, d).

Compound 7: N-[(1-methyl-2-Trifluoromethylindol-5-yl)methyl]-6-(trifluoromethyl)-3-Pyridinecarboxamide

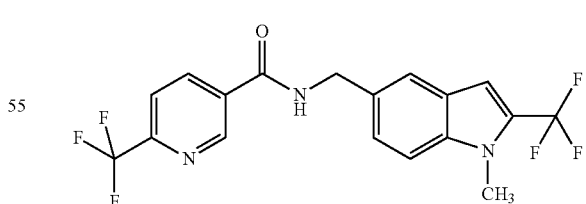

[(1-Methyl-2-trifluoromethylindol-5-yl)methyl]amine (Intermediate 11, 150 mg, 0.657 mmol) was dissolved in DCM (10 mL) and 6-(trifluoromethyl)nicotinoyl chloride (ABCR; 165 mg, 0.789 mmol) was added. Et$_3$N (0.183 mL, 1.315 mmol) was added and the reaction mixture was left to stir at room temperature for 2 hrs. The reaction mixture was quenched with methanol (10 mL) and evaporated to dryness.

The resulting residues were partitioned between ethyl acetate and a 1M solution of citric acid. The organic layer was collected, dried (MgSO$_4$), filtered and the solvent removed. The resulting residues were then purified by MDAP and evaporated to dryness to give the title compound (100 mg);

m/z (ES$^+$) 402 (M+1); $^1$H NMR (400 MHz, d6-DMSO): δ 9.50 (1H, t), 9.20 (1H, d), 8.51 (1H, dd), 8.06 (1H, d), 7.67 (1H, s), 7.62 (1H, d), 7.39 (1H, dd), 7.10 (1H, s), 4.63 (2H, d), 3.85 (3H, s).

Biological Assay

The PAM activity of the compounds of the invention at the α7 nAChR may be determined using the following cell-based calcium flux assay which uses a Fluorimetric Image Plate Reader (FLIPR) (see Schroeder et al.; J. Biomolecular Screening, 1(2), p 75-80, 1996).

GH4C1 cell line stably transfected with human α7 nAChR was suspended in a 384 well plate and incubated at 30° C. for 48 h in a 5% carbon dioxide atmosphere. The growth media was removed and the cells washed three times with a solution of Hanks' balanced salt solution (HBSS), 20 mM HEPES and 2.5 mM probenecid leaving 20 μl washing solution in each well. A loading solution (20 μl) containing HBSS, probenecid, 1-4 μM Fluo4 AM (a calcium indicator dye) and pluronic acid was added and the plate incubated for 45 min at 37° C. under an atmosphere free from carbon dioxide. The cells were washed three times leaving 30 μl in each well. The plate containing the cells and calcium indicator dye were then transferred to the FLIPR. The assay was initiated by collecting baseline datapoints at 10 second intervals followed by addition of the test compound in buffer solution (0.33% DMSO) and diluted to a final concentration of 10 μM and serial dilution of the wells, 1:2 or 1:3, gave a low concentration of <1 nM. Following a further 5-10 mins 10 μl of 50 μM nicotine was added and data collected for 2-3 mins. Nicotine produced a rapid, transient and reproducible calcium flux which could be potentiated with the positive allosteric modulator test compounds.

The supporting compounds were screened using the assay described above and gave gave a pEC$_{50}$ of equal to or greater than 6.0 with a maximum potentiation of the response area to approximately 1200% relative to nicotine control.

Supporting compound 1 was screened using the assay described above and gave a pEC$_{50}$ of greater than 6 with a maximum potentiation of the response area to approximately 1200% relative to nicotine control.

In vivo assays with utility for the evaluation of activity of nicotinic α7 receptor positive modulators include, but are not limited to: cognition assays in both naïve and pharmacologically-impaired animals including delayed matching and non-matching to position, passive avoidance, novel object recognition, Morris water maze (or variants thereof), radial arm maze, five choice serial reaction time task, and cued/contextual fear conditioning; sensory gating assays in both naïve and pharmacologically-impaired animals including pre-pulse inhibition of the startle reflex and auditory gating; and assays of drug- (e.g. amphetamine, morphine, phencyclidine) induced locomotor activity.

The invention claimed is:

1. A compound of formula (I) or a salt thereof:

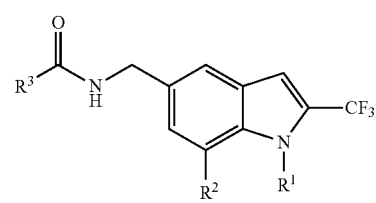

(I)

wherein:
R$^1$ is hydrogen or C$_{1-3}$alkyl;
R$^2$ is hydrogen, halo or cyano; and
R$^3$ is group

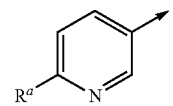

wherein R$^a$ is halo, C$_{1-6}$alkyl, C$_{1-6}$alkoxy, haloC$_{1-6}$alkyl, haloC$_{1-6}$alkoxy or cyano.

2. The compound according to claim 1 or a salt thereof, wherein R$^1$ is hydrogen.

3. The compound according to claim 1 or a salt thereof, wherein R$^2$ is hydrogen.

4. A compound which is:
N-[(2-trifluoromethyl-1H-indol-5-yl)methyl]-6-(trifluoromethyl)-3-pyridinecarboxamide;
N-[(2-trifluoromethyl-1H-indol-5-yl)methyl]-6-(2,2,2-trifluoroethoxy)-3-pyridinecarboxamide;
6-bromo-N-{[2-(trifluoromethyl)-1H-indol-5-yl]methyl}-3-pyridinecarboxamide;
6-cyano-N-{[2-(trifluoromethyl)-1H-indol-5-yl]methyl}-3-pyridinecarboxamide;
N-[(2-trifluoromethyl-7-bromo-1H-indol-5-yl)methyl]-6-(trifluoromethyl)-3-pyridinecarboxamide;
N-[(2-trifluoromethyl-7-cyano-1H-indol-5-yl)methyl]-6-(trifluoromethyl)-3-pyridinecarboxamide;
N-[(1-methyl-2-trifluoromethylindol-5-yl)methyl]-6-(trifluoromethyl)-3-pyridinecarboxamide; or
a salt thereof.

5. The salt according to claim 1, wherein the salt is a pharmaceutically acceptable salt.

6. A compound which is N-[(2-Trifluoromethyl-1H-indol-5-yl)methyl]-6-(trifluoromethyl)-3-pyridinecarboxamide.

7. A method of treating a psychotic disorder in a human comprising administering an effective amount of a compound as defined in claim 1 or a pharmaceutically acceptable salt thereof.

8. A method of treating schizophrenia in a human comprising administering an effective amount of a compound as defined in claim 1 or a pharmaceutically acceptable salt thereof.

9. A method of treating cognitive impairment in a human comprising administering an effective amount of a compound as defined in claim 1 or a pharmaceutically acceptable salt thereof.

10. A pharmaceutical composition comprising: a) a compound as defined in claim 1 or a pharmaceutically acceptable salt thereof; and b) one or more pharmaceutically acceptable carriers or excipients.

11. The method according to claim 7, wherein the psychotic disorder is schizophrenia.

* * * * *